(12) United States Patent
Lario Garcia et al.

(10) Patent No.: US 8,465,483 B2
(45) Date of Patent: Jun. 18, 2013

(54) CIRCUIT FOR RADIOFREQUENCY DEVICES APPLICABLE TO LIVING TISSUES AND DEVICE CONTAINING SAME

(75) Inventors: Javier Lario Garcia, Barcelona (ES); José Calbet Benach, Barcelona (ES); Jorge Buisan Escartin, Barcelona (ES)

(73) Assignee: Indiba, S.A., Barcelona (ES)

( * ) Notice: Subject to any disclaimer, the term of this patent is extended or adjusted under 35 U.S.C. 154(b) by 728 days.

(21) Appl. No.: 12/665,180

(22) PCT Filed: May 26, 2008

(86) PCT No.: PCT/ES2008/000372
§ 371 (c)(1),
(2), (4) Date: Dec. 17, 2009

(87) PCT Pub. No.: WO2008/155433
PCT Pub. Date: Dec. 24, 2008

(65) Prior Publication Data
US 2010/0198213 A1    Aug. 5, 2010

(30) Foreign Application Priority Data
Jun. 20, 2007 (ES) .................. 200701702

(51) Int. Cl.
*A61B 18/18* (2006.01)
(52) U.S. Cl.
USPC ............................................. 606/34; 606/41
(58) Field of Classification Search
USPC ............................................. 606/32, 34, 41
See application file for complete search history.

(56) References Cited

U.S. PATENT DOCUMENTS

| | | | | |
|---|---|---|---|---|
| 2,005,083 | A | | 6/1935 | Hansell |
| 3,808,465 | A | * | 4/1974 | Banks ........................... 327/129 |
| 4,012,705 | A | * | 3/1977 | Prevot .......................... 333/167 |
| 4,209,018 | A | | 6/1980 | Meinke et al. |
| 4,306,200 | A | * | 12/1981 | Takayama ..................... 330/277 |
| 4,510,464 | A | * | 4/1985 | Takahashi .................. 331/116 R |
| 4,571,560 | A | * | 2/1986 | Dobrovolny .................. 333/174 |
| 4,615,330 | A | | 10/1986 | Nagasaki et al. |
| 5,187,457 | A | | 2/1993 | Chawla et al. |
| 5,300,068 | A | * | 4/1994 | Rosar et al. ..................... 606/34 |

(Continued)

FOREIGN PATENT DOCUMENTS

| | | |
|---|---|---|
| DE | 3514676 | 10/1986 |
| EP | 0 854 564 B1 | 7/1998 |

(Continued)

OTHER PUBLICATIONS

Supplemental European Search Report dated Apr. 12, 2011, issued in the corresponding European Application No. 08775400.8-2215.

(Continued)

*Primary Examiner* — Linda Dvorak
*Assistant Examiner* — Jocelyn D Ram
(74) *Attorney, Agent, or Firm* — RatnerPrestia

(57) ABSTRACT

The supply circuit for the electrodes comprises a series resonant filter and a parallel resonant filter, tuned to admit the fundamental signal of the input signal and simultaneously and exponentially attenuate the remaining harmonics by increasing the frequency thereof, in such a way that the input signal with harmonics only passes the fundamental signal without attenuation to the output, while the harmonics causing interferences are increasingly attenuated as their frequency is raised.

7 Claims, 3 Drawing Sheets

U.S. PATENT DOCUMENTS

| | | | | |
|---|---|---|---|---|
| 5,550,438 A * | 8/1996 | Reijnaerts | ................ | 315/219 |
| 5,642,065 A * | 6/1997 | Choi et al. | ................ | 327/110 |
| 5,907,242 A | 5/1999 | Gard | | |
| 6,238,387 B1 * | 5/2001 | Miller, III | ................ | 606/34 |
| 6,565,558 B1 * | 5/2003 | Lindenmeier et al. | ................ | 606/34 |
| 6,961,251 B2 | 11/2005 | Porter et al. | | |
| 2004/0008527 A1 | 1/2004 | Honda | | |
| 2004/0138654 A1 * | 7/2004 | Goble | ................ | 606/34 |
| 2007/0173810 A1 * | 7/2007 | Orszulak | ................ | 606/37 |
| 2008/0143433 A1 | 6/2008 | Kuepfer et al. | | |
| 2009/0157073 A1 * | 6/2009 | Orszulak | ................ | 606/34 |
| 2011/0069518 A1 * | 3/2011 | Shin et al. | ................ | 363/140 |
| 2011/0172656 A1 * | 7/2011 | Schall et al. | ................ | 606/34 |

FOREIGN PATENT DOCUMENTS

| | | |
|---|---|---|
| ES | 253731 | 11/1958 |
| WO | WO 96/39085 | 12/1996 |
| WO | WO 2006/084505 A1 | 8/2006 |

OTHER PUBLICATIONS

Supplementary European Search Report dated Nov. 25, 2011, issued in the corresponding European Patent Application No. 08775400.8-2215.

International Search Report (PCT/ISA/210) dated Sep. 19, 2008 for PCT/ES2008/000372.

Gerhard, Surgical Electrotechnology: Quo Vadis? IEEE Transactions on Biomedical Engineering, (1984), vol. BME-31, No. 12, pp. 787-792.

Search Report dated Aug. 19, 2010, issued in the corresponding Singapore Patent Application No. 2009083742.

* cited by examiner

CIRCUIT FOR RADIOFREQUENCY DEVICES APPLICABLE TO LIVING TISSUES AND DEVICE CONTAINING SAME

SUBJECT-MATTER OF THE INVENTION

The present invention relates to a novel circuit for radiofrequency devices applicable to living tissues, which also includes devices for diathermy by conduction current of different types and electroscalpels which incorporate the circuit according to the present invention, said circuit having substantial features of novelty and inventive step allowing significant advantages to be obtained over what is known at present.

In particular, the circuit for diathermy devices by conduction and for electroscalpels according to the present invention allows the harmonics of a non-sinusoidal signal to be attenuated, allowing a sinusoidal signal to be obtained at the output of a high-efficiency amplifier in order to comply with electromagnetic compatibility (EMC) standards which are mandatory in practically all countries in the world.

As is known, EMC is the property by which an electronic appliance does not interfere with and is not interfered by other electronic appliances, when they are all operating correctly.

BACKGROUND OF THE INVENTION

Diathermy is the use of special electrical currents to raise the temperature of living tissue for therapeutic purposes. It is sometimes known as hyperthermy, particularly in the medical sector.

Equipment for diathermy by conduction current is very effective in many applications in the field of electromedicine and electroaesthetics. Electroscalpels are also sometimes referred to as diathermy appliances.

It is advantageous for diathermy equipment and electroscalpels to work with high-efficiency amplifiers (from the point of view of energy consumption), but in these circumstances they usually emit multiple electromagnetic signals due fundamentally to parasitic elements which interfere with other electronic pieces of equipment.

These pieces of equipment for diathermy by conduction and electroscalpels usually function with sinusoidal signals like the one in FIG. 1. FIG. 2 shows the frequency spectrum of the signal of FIG. 1 using the Fourier transform which is another way of representing the signal in the frequency domain, the X axis showing the frequency and the Y axis showing the amplitude of the signal.

The increase of temperature of the living tissue by diathermy is obtained by transmitting energy to the tissue by two methods: by induced currents (electrodes not in contact with the tissue) or by conduction currents (electrodes in contact with the tissue).

In general, the signal frequency applied in the contactless connection method must be very much higher than the signal frequency applied in the contact connection method.

In diathermy by conduction two electrodes are contacted with the living tissue in such a way that a current flow occurs between the two electrodes and passes through the tissue that it encounters in its passage. The current flowing through the tissue causes the temperature to rise by the Joule effect, due to the electrical resistance of said tissue.

In equipment for diathermy by conduction the electrodes are connected by contact. There are two application methods: one is known as the capacitive method and the other as the resistive method.

The electrodes used in diathermy by conduction are normally asymmetric. In this case, and due to the current density, the greatest rise in temperature occurs in the tissue nearest the active electrode (the smaller one). In the capacitive method, the two electrodes are metal, but one of them has an insulating layer. In the resistive method, the two electrodes are metal with no insulation.

In electrosurgical equipment, such as electroscalpels, the current density is so high at the point of contact between the active electrode and the tissue that cutting, coagulation or fulguration of the tissue occurs.

It is very difficult to comply with EMC standards mentioned above when using this type of equipment. In fact, standard IEC 60601-2-2, which must be met by electroscalpels, states that EMC tests must be carried out with the equipment connected, but with the output power at zero, since, at the time, it was accepted that it was very difficult to comply with EMC standards when the electroscalpel is used for cutting, fulguration or coagulation, and since the equipment is used during a surgical operation for a relatively short time and the benefit to the patient is very high.

Equipment for diathermy by conduction operate in a similar way to an electroscalpel, but with a much larger active electrode, so that the current density J in the contact area with the tissue is much lower, whereas the current I which flows through the tissue (of up to 3 A effective R.M.S. value), the output voltage V (of up to 800 V of effective R.M.S. value) and the signal frequency (between 0.4 MHz and 3 MHz) are of approximately the same order of magnitude. From the EMC point of view, these voltages, currents and frequencies are relatively high, and make it very difficult to comply with the EMC standards in different countries. As there are no specific standards for this type of equipment, as there are for electroscalpels, equipment for diathermy by conduction must meet the general EMC standard for medical equipment, EN 60601-1-2 in Europe. This states that EMC must be measured with the equipment in the worst possible condition, which is, at the maximum output power, unlike electroscalpels which must be measured with the power at zero, which is a very much easier situation in which to meet the EMC requirements.

Any pure and periodic non-sinusoidal signal may be broken down into multiple sinusoidal signals known as harmonics (of differing frequency, amplitude and phase), which can be calculated from the Fourier transform of the periodic signal.

A method for minimising electromagnetic interference consists of the signal on which the amplifier works being pure sinusoidal, for example a class A amplifier, but in this case the maximum theoretical efficiency is 50% with the consequent energy loss and heating of the equipment.

Some high-efficiency amplifiers such as those in class C, D, E or F, for example, may lead to theoretical efficiencies of up to 100%. These amplifiers are based on generating a signal that ideally is squared (but may be trapezoidal or quasi-trapezoidal) or a pulse signal, and filtering the fundamental signal with the intention of achieving maximum attenuation of undesired harmonics, normally with a second order LC filter, which may be serial or parallel, but no filter has been described in the prior art like the one described in this patent for this type of amplifier.

In practice, the efficiency of these amplifiers is less than the theoretical efficiency due to losses in the components and/or to non-matching of impedances.

FIG. 3 shows a squared signal. FIG. 4 shows that the frequency spectrum of said squared signal contains many other higher frequency signals (harmonics). These signals are undesired because they may connect to the network cable or because they may emit in the form of radiation through the patient's cables, which may more easily cause electromagnetic interference in other equipment.

SUMMARY OF THE INVENTION

The present invention relates to a circuit which allows diathermy equipment to meet the EMC requirements of different countries more easily, particularly in radiated and conducted emission tests.

The circuit may be used in electrosurgical equipment and electroscalpels as well as in equipment for diathermy by conduction.

The object of the present invention is to attenuate undesired signals as far as possible, so that the equipment does not interfere with other electronic equipment when a generator of squared, trapezoidal, pulse or any other signal that contains harmonics is used as the main source of the signal.

The circuit consists of two resonant filters, one serial and the other parallel optionally separated by a transformer (which may have a turns ratio of 1:N, where N is a real number, which may be greater than unity if the fundamental signal of the input signal is to be amplified, or less than unity if the fundamental signal of the input signal is to be attenuated, or equal to unity if it is only to be isolated), which allow the fundamental signal of the input signal (a sinusoidal signal) to pass through, the circuit in its entirety attenuating the rest of the harmonics as the frequency thereof increases. This type of diathermy equipment usually has a condenser at its output, known as an anti-stimulus condenser to ensure that the non-linear effects produced by high voltages (electric arcs) do not cause a demodulation that may generate low frequencies (which could cause fibrillation for example during a procedure using an electroscalpel, IEC 60601-2-2).

Said anti-stimulus condensers cause a fall in voltage and, to avoid this, provision is made to incorporate an inductance with a value such that, serially with the anti-stimulus condenser, the resonance frequency of the unit is the fundamental frequency of the input signal. An additional effect is thereby achieved, which is that the very high frequencies are attenuated due to said inductance, thus reducing the level of emissions radiated through the patient's cables.

These and other features will be better understood from the detailed description which follows, and from the accompanying drawings showing graphs of the signals normally used and an embodiment of the invention, given as a non-limiting example.

DETAILED DESCRIPTION

Figure 5:
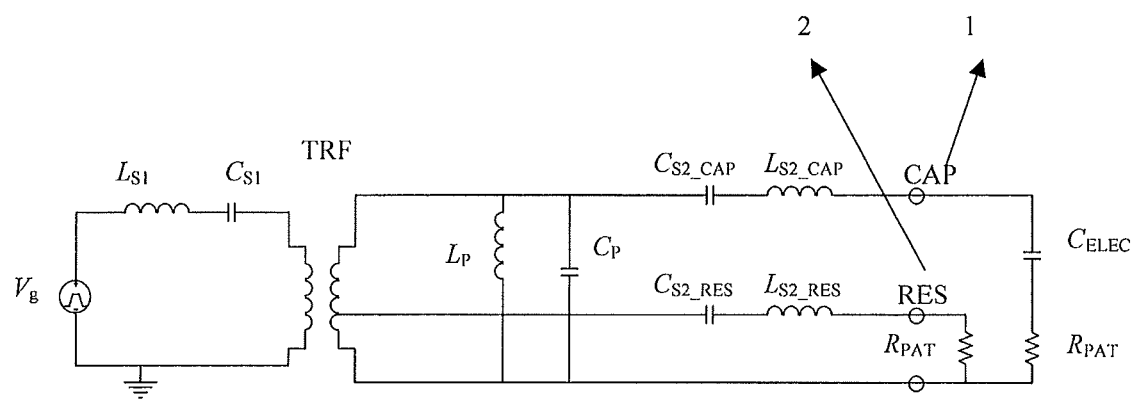
FIG. 5 shows a diagram of the circuit according to the invention, where 1 indicates the capacitive output (CAP) and 2 indicates the resistive output (RES).

With reference to FIG. 5, the present invention comprises a circuit for equipment for diathermy by conduction consisting of two resonant filters, one serial and the other parallel, which are tuned to allow the fundamental signal of the input signal which contains harmonics to pass through (this fundamental signal is a sinusoidal signal) and which exponentially attenuate the rest of the harmonics as the frequency of said harmonics increases.

The serial filter consists of the inductance $L_{S1}$ and a capacitance $C_{S1}$, and offers very low impedance (in fact almost a short circuit) to the fundamental frequency of the input signal, and a high impedance to the rest of the harmonics of the input signal as the frequency thereof rises.

The parallel filter consists of the inductance $L_P$ and a capacitance $C_P$, and offers very high impedance (in fact practically an open circuit) to the fundamental frequency of the input signal, and low impedance to the rest of the harmonics of the input signal as the frequency of said harmonics rises.

The fundamental signal of the signal with harmonics (a sinusoidal signal) will therefore pass with practically no attenuation to the output, whereas the resonant serial and parallel filters will increasingly attenuate the harmonics which cause interference as the frequency of said harmonics increases, thus facilitating compliance with the EMC standards.

A transformer TRF may optionally be inserted between the resonant serial filter consisting of $L_{S1}$ and $C_{S1}$ and the resonant parallel filter consisting of $L_P$ and $C_P$, with a turn ratio of 1:N, where N is a real number which may be greater than unity if the fundamental signal of the input signal is to be amplified, or less than unity if the fundamental signal of the input signal is to be attenuated, or equal to unity if it is only to be isolated. The transformer may also be dispensed with.

The inductance of the resonant parallel filter $L_P$ may be an independent inductance or the parasitic inductance of the secondary winding/coil of the transformer TRF if present.

The proposed circuit is suitable for application to electrosurgical equipment such as electroscalpels, to equipment for diathermy by conduction with an insulated active metal electrode (capacitive mode, see Spanish patent 287 964 from the same applicant), to equipment for diathermy by conduction with a dual electrode: an insulated active metal electrode (capacitive mode) and with an active metal electrode (resistive mode, see Spanish patent 2 139 507 from the same applicant), and to equipment for diathermy by conduction with an active metal electrode. This type of equipment has a return or neutral electrode with a greater area than the active electrode. The circuit is also suitable for diathermy equipment such as that known as bipolar, in which both electrodes behave as active electrodes, are close to one another and are of similar size.

The equipment for diathermy by conduction described above usually has at its output a condenser $C_{S2\_CAP}$ (and $C_{S2\_RES}$ if the system has a resistive output, which is an active electrode without insulation), known as an anti-stimulus condenser to ensure that the electric arcs produced by high voltages do not cause low frequency currents through the demodulation effect. These low frequency currents (f<10 kHz) may cause nerve stimulation or muscle contraction when the diathermy appliance is used.

The capacitance value of the anti-stimulus condenser is usually low (approximately a few nF), which causes a fall in voltage depending on its value ($C_{S2\_CAP}$ and/or $C_{S2\_RES}$), and in the current/flowing through it.

A feature of the invention is that to avoid this fall in voltage, it is proposed to place an inductance ($L_{S2\_CAP}$ and/or $L_{S2\_RES}$) serially with the anti-stimulus condenser ($C_{S2\_CAP}$ and/or $C_{S2\_RES}$ respectively) with a value such that it causes its resonance frequency to be equal to the fundamental frequency of the input signal. This causes the impedance of the network LC to be practically nil at the fundamental frequency of the input signal. Moreover, an additional effect is thereby achieved, in that the very high frequencies are attenuated due to said inductance ($L_{S2\_CAP}$ and/or $L_{S2\_RES}$), thus reducing still further the level of emissions radiated through the patient's cables and through the network cable.

The values of the circuit components are independent of the output power. The values of each network LC of the circuit are a function of the work frequency corresponding to the formula (1)

$$f_0 = \frac{1}{2\pi\sqrt{LC}} \quad (1)$$

To achieve maximum amplifier efficiency, the output frequency may vary depending on the impedance of the electrode-plus-patient unit, and therefore the circuit and/or frequency may be tuned to match the impedances of the output circuit to the impedance of the electrode-plus-patient unit.

The typical frequency margin of the output signal for this type of equipment may be between 100 kHz and 10 MHz, so that no nerve stimulation occurs, and its value is not fundamental to the correct functionality of the circuit.

Figure 1:
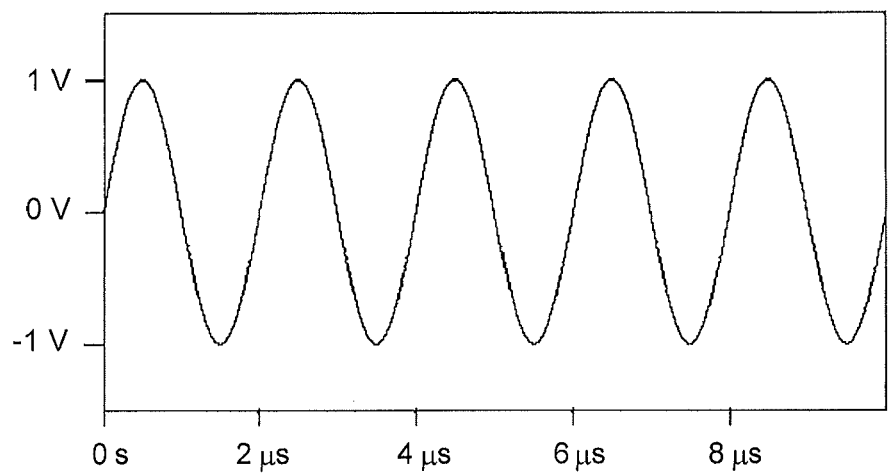
FIG. 1 shows an illustration of a sinusoidal signal (for example of 500 kHz, normalised at a unitary amplitude).
Figure 2:
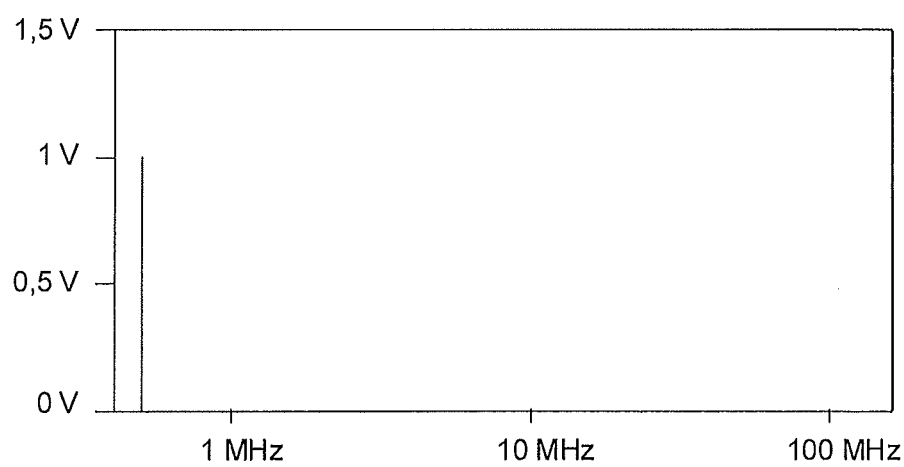
FIG. 2 shows the frequency spectrum of the signal of FIG. 1 using the Fourier transform, which is another way of representing FIG. 1, changing time (FIG. 1) for frequency on the X axis, the Y axis being the signal amplitude.
Figure 3:
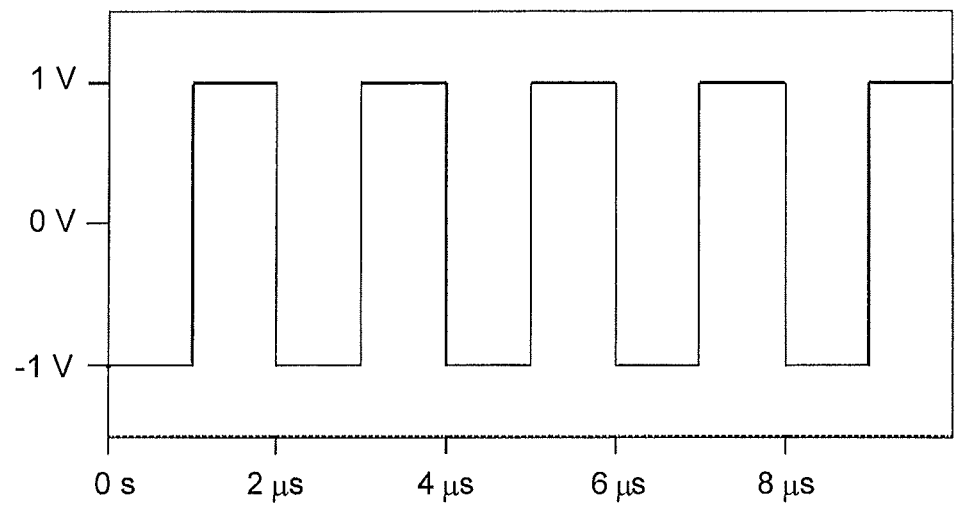
FIG. 3 shows a squared signal.
Figure 4:
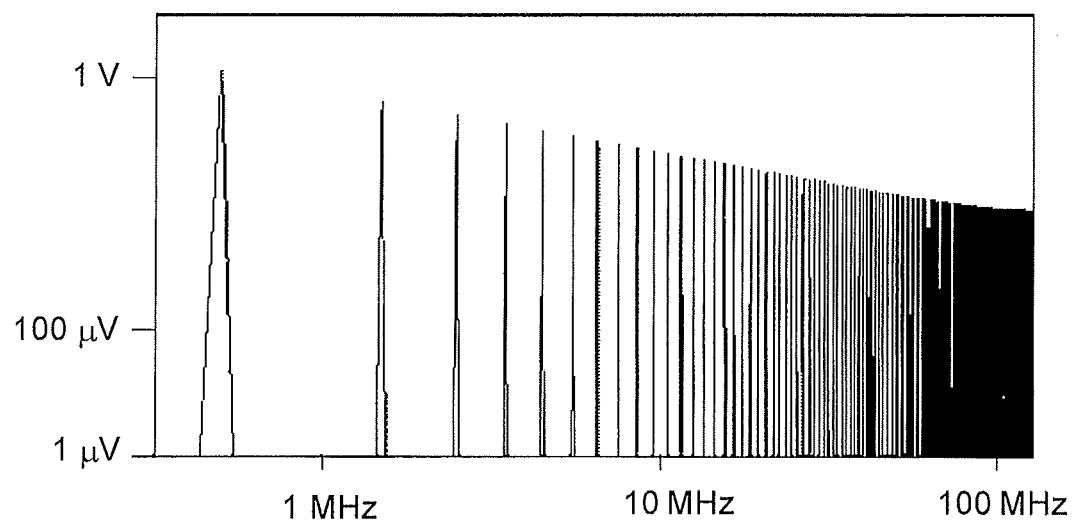
FIG. 4 shows the frequency spectrum of the signal of FIG. 3 using the Fourier transform. It can be seen that the squared signal contains other mixed signals at higher frequencies (harmonics) which may potentially cause interference. The X and Y axes have a logarithmic scale.
Figure 6:
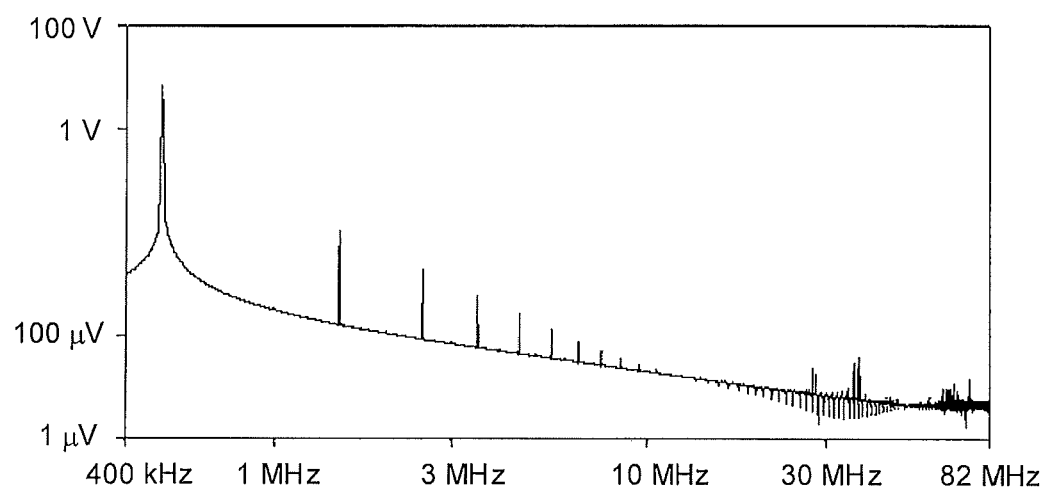
In FIG. 6 it can be seen that at the output of the filter in the patient's resistance ($R_{PAT}$) the harmonics are substantially attenuated, as desired.

A practical embodiment, which is cited solely as a non-limiting example of the scope of the present invention, can be seen in FIG. 5. FIG. 6 shows how the high frequency harmonics have been attenuated when compared with the spectrum of the squared input signal (FIG. 4).

Clearly, the present invention will be applicable to radiofrequency equipment applicable to living tissues, such as equipment for diathermy by conduction: solely capacitive equipment (with an active metal electrode with an insulating layer), solely resistive equipment (with the active metal electrode), or capacitive and resistive equipment with the active electrode smaller than the passive electrode, bipolar equipment (with similar electrodes) and electroscalpels. In FIG. 5, 1 indicates the capacitive output (CAP) and 2 indicates the resistive output (RES).

It will be understood that the invention has been explained above simply as a non-limiting example and many variants may be introduced within the scope of the invention which is defined by the following claims.

The invention claimed is:

1. A circuit for supplying output electrodes of a radiofrequency device applicable to living tissues, said circuit comprising:
    a transformer having a primary winding, a secondary winding, and a turn ratio of 1:N, where N is a real number;
    a resonant serial filter connected to the primary winding of the transformer having an inductor $L_{S1}$ connected in series with a capacitor $C_{S1}$; and
    a resonant parallel filter connected to the secondary winding of the transformer having an inductor $L_p$ connected in parallel with a capacitor $C_P$;
    wherein the resonant serial filter and the resonant parallel filter allow a fundamental signal of an input signal, which includes harmonics, to simultaneously pass through and exponentially attenuate the harmonics as a frequency of said harmonics increases, and
    wherein an output frequency of said circuit is varied such that a combined impedance of a plurality of output electrodes connected to the circuit, and living tissue in contact with the output electrodes matches an impedance of the circuit.

2. The circuit of claim 1, wherein the inductor $L_P$ of the resonant parallel filter is the parasitic inductance of the secondary winding of the transformer.

3. The circuit of claim 1 including anti-stimulus capacitors $C_{S2\_CAP}$, $C_{S2\_RES}$ at each output electrode, each of said anti-stimulus capacitors $C_{S2\_CAP}$, $C_{S2\_RES}$ having a corresponding inductor $L_{S2-CAP}$, $L_{S2-RES}$ connected in series, the inductors $L_{S2-CAP}$, $L_{S2-RES}$ having values that resonate at a fundamental frequency of the input signal.

4. The circuit of claim 1, wherein the inductor $L_{S1}$ and the capacitor $C_{S1}$ of the resonant serial filter have a first impedance to the fundamental frequency of the input signal and a second impedance to the harmonics of the input signal, the first impedance being lower than the second impedance.

5. The circuit of claim 1, wherein the inductor $L_P$ and the capacitor $C_p$ of the resonant parallel filter have a first impedance to the fundamental frequency of the input signal and a second impedance to the harmonics of the input signal, the first impedance being higher than the second impedance.

6. The circuit of claim 1, wherein the radiofrequency device is a diathermy device.

7. The circuit of claim 1, wherein the radiofrequency device is an electroscalpel device.

* * * * *